United States Patent [19]
Weinberger

[11] Patent Number: 5,503,613
[45] Date of Patent: Apr. 2, 1996

[54] APPARATUS AND METHOD TO REDUCE RESTENOSIS AFTER ARTERIAL INTERVENTION

[75] Inventor: Judah Z. Weinberger, Teaneck, N.J.

[73] Assignee: The Trustees of Columbia University in the City of New York, New York, N.Y.

[21] Appl. No.: 184,380

[22] Filed: Jan. 21, 1994

[51] Int. Cl.$^6$ .................................................. A61N 5/00
[52] U.S. Cl. ................................................ 600/3; 128/659
[58] Field of Search ..................... 600/1–8; 128/656–659

[56] References Cited

U.S. PATENT DOCUMENTS

| | | | |
|---|---|---|---|
| 3,324,847 | 6/1967 | Zoumboulis | 128/1.2 |
| 3,811,426 | 5/1974 | Culver et al. | 128/1.2 |
| 3,927,325 | 12/1975 | Hungate et al. | 250/435 |
| 4,770,653 | 9/1988 | Shturman | 604/21 |
| 5,106,360 | 4/1992 | Ishiwara et al. | 600/3 |
| 5,199,939 | 4/1993 | Dake et al. | 600/3 |
| 5,213,561 | 5/1993 | Weinstein et al. | 600/7 |
| 5,302,168 | 4/1994 | Hess | 600/3 |

FOREIGN PATENT DOCUMENTS 1065989  9/1959  Germany ........................... 600/8

OTHER PUBLICATIONS

Joseph Wiedermann, Jeffrey Leavy, Howard Amols, Allan Schwartz, Shunichi Homma, Charles Marboe, Judah Weinberger; "Effects of High Dose Intracoronary Irradiation on Vasomotor Function and Smooth Muscle Histopathology". AHA, Oct. 1992.

Joseph G. Widermann, Charles Marboe, Howard Amols, Allan Schwartz, Judah Weinberger; "Intracoronary Irradiation Markedly Reduces Restenosis After Balloon Angioplasty in a Porcine Model". AHA, Oct. 1993.

Primary Examiner—Angela D. Sykes
Assistant Examiner—John Lacyk
Attorney, Agent, or Firm—John P. White

[57] ABSTRACT

An apparatus guided by a guidewire within a patient's artery for reducing restenosis after arterial intervention in the patient's artery. A radiation dose delivery wire with a radiation source encapsulated within its distal end is inserted into a blind lumen in a balloon catheter to deliver radiation to a target area of the patient's artery.

17 Claims, 10 Drawing Sheets

APPARATUS AND METHOD TO REDUCE RESTENOSIS AFTER ARTERIAL INTERVENTION

BACKGROUND OF THE INVENTION

The present invention relates to an apparatus and a method to reduce restenosis after arterial intervention.

Restenosis after arterial intervention in general, and percutaneous transluminal coronary angioplasty ("PTCA") in particular, is primarily due to medial smooth muscle cell proliferation.

Figure 1:
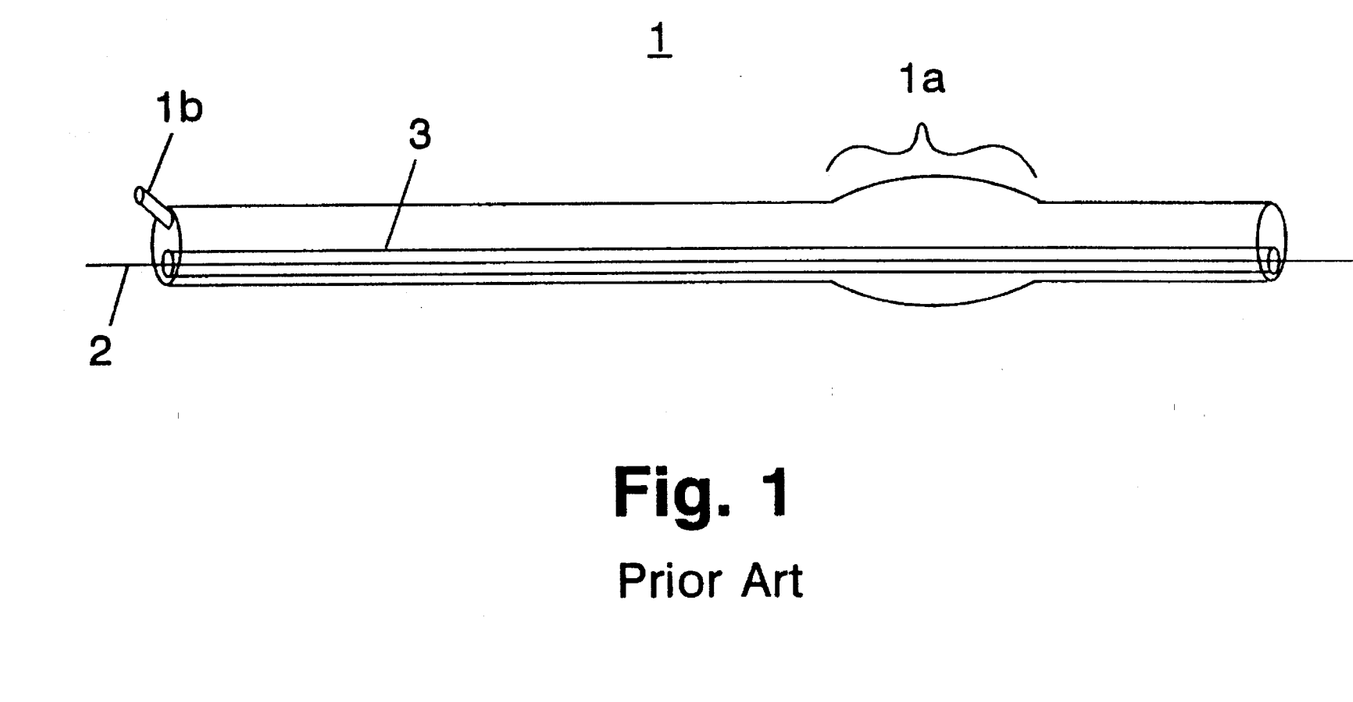
FIG. 1 shows the construction of a conventional over-the-rail type balloon catheter.

Conventional PTCA is performed using a balloon catheter such an over-the-wire type catheter manufactured, for example, by Scimed Life Systems, Inc, of Maple Grove, Minn. or a mono-rail type catheter manufactured, for example, by Advanced Cardiovascular Systems, Inc, of Temecula, Calif. FIG. 1 depicts such a conventional over-the-wire balloon catheter 1. The conventional balloon catheter 1 is utilized in an angioplasty procedure as follows. A conventional guidewire 2 is inserted into the patient's artery until the distal end of the guidewire 2 is past a target area (not shown) of the artery (not shown) where there is a buildup of material. The conventional balloon catheter 1 has a lumen 3 running therethrough. The guidewire 2 is inserted into the distal end of the balloon catheter 1 and the balloon catheter 1 is advanced over the guidewire until the balloon section 1a of the balloon catheter 1 is adjacent the buildup of material, The balloon section 1a is then inflated by an inflation means (not show) connected to an inflation port 1b to clear the artery. Finally, the balloon section 1a is deflated, the balloon catheter 1 is pulled back up the guidewire and removed and the guidewire is likewise removed from the patient's artery.

Current technology contemplates two distinct design classes for devices for the prevention of restenosis after arterial interventions. The first design class, an arterial stent type device, is designed for long term deployment within the artery. Such a stent, if designed to emit radiation, would be in place long after the time necessary for the prevention of smooth muscle cell proliferation at the arterial site. U.S. Pat. No. 5,059,166 to Fischell describes such a long term stent.

The second design class for restenosis preventing devices contemplates the delivery of unspecified doses of radiation via radioactive catheters and guidewires. These devices utilize a movable, flexible radiation shield. However, it is questionable whether such a radiation shield could be constructed given the thickness of material required to shield the radiation source and the flexibility required to allow delivery of the radiation source and shield to the coronary site. U.S. Pat. No. 5,213,561 to Weinstein relates to a device of this class.

In addition, neither class of devices addresses the need to isolate the radioactive source from contact with the patient's body fluids.

SUMMARY OF THE INVENTION

It is an object of the present invention to provide an arrangement for reducing restenosis after arterial intervention in a patient's artery. Such arterial intervention includes, but is not limited to, balloon angioplasty, atherectomy, and stent placement.

It is a further object of the present invention to provide an arrangement for reducing restenosis after arterial intervention in the patient's artery by delivering a precise dosage of radiation to the patient's artery at a target area.

It is a further object of the present invention to provide an arrangement for reducing restenosis after arterial intervention in the patient's artery by delivering a precise radioactive dosage to the patient's artery at a target area while eliminating contact between the radioactive source and the patient's body fluids.

It is a further object of the present invention to provide an arrangement for reducing restenosis after arterial intervention in the patient's artery by delivering a precise radioactive dosage to the patient's artery at a target area while shielding a doctor and other staff from over-exposure to radiation.

According to one aspect of the present invention, an apparatus guided by a guidewire within a patient's artery for reducing restenosis after arterial intervention in the patient's artery is provided, comprising a radiation dose delivery wire with a radiation source encapsulated within its distal end, and a balloon catheter with a blind lumen sealed at its distal end and a guidewire lumen extending therethrough to accept said guidewire, said blind lumen being adapted to accept said radiation delivery wire into its proximal end.

According to another aspect of the present invention, an apparatus inserted into a sheath in a patent's artery and guided by a guidewire within the patient's artery for reducing restenosis after arterial intervention in the patient's artery is provided, comprising a radiation dose delivery wire with a radiation source encapsulated within its distal end, and a balloon catheter with a blind lumen sealed at its distal end and a guidewire lumen extending therethrough to accept said guidewire, said blind lumen being adapted to accept said radiation dose delivery wire into its proximal end, said balloon catheter being adapted to be inserted into said sheath.

According to another aspect of the present invention, an apparatus guided by a guidewire within a patient's artery for reducing restenosis after arterial intervention in the patient's artery is provided, comprising a radiation dose delivery wire with a radiation source encapsulated within its distal end, and a balloon catheter with a blind lumen sealed at its distal end and a guidewire lumen extending partially through said balloon catheter, said blind lumen being adapted to accept said radiation dose delivery wire into its proximal end, said guidewire lumen having an entry port located at a distal end of said balloon catheter and an exit port located upon a circumferential surface of said balloon catheter.

According to another aspect of the present invention, an apparatus for reducing restenosis after arterial intervention in a patient's artery is provided, comprising a guidewire for insertion into the patient's artery at least as far as a target area of the artery, a radiation dose delivery wire with a radiation source encapsulated within its distal end, and a balloon catheter with a blind lumen sealed at its distal end and a guidewire lumen extending therethrough to accept said guidewire, said blind lumen being adapted to accept said radiation delivery wire into its proximal end.

According to another aspect of the present invention, an apparatus guided by a guidewire within a patient's artery for reducing restenosis after arterial intervention in the patient's artery is provided, comprising a radiation dose delivery wire with a radiation source encapsulated within its distal end, and a catheter with a blind lumen sealed at its distal end and a guidewire lumen extending therethrough to accept said guidewire, said blind lumen being adapted to accept said radiation delivery wire into its proximal end.

According to another aspect of the present invention, an apparatus to be inserted into a catheter for reducing restenosis after arterial intervention in a patient's artery is provided, comprising a radiation dose delivery wire with a radiation source encapsulated within its distal end, and a blind lumen open at its proximal end and sealed at its distal end, said blind lumen being adapted to accept said radiation dose delivery wire into its proximal end and to be inserted into said catheter.

According to another aspect of the present invention, a method of reducing restenosis after arterial intervention in a patient's artery is provided, comprising inserting a guidewire into the patient's artery until a distal end of the guidewire is at least as far into the artery as a predetermined section of the artery, inserting the guidewire into a guidewire lumen of a balloon catheter with a blind lumen, inserting the balloon catheter with the blind lumen into the patient's artery at least as far as the predetermined section of the artery, inserting a radiation dose delivery wire into said blind lumen in said balloon catheter, moving said radiation dose delivery wire a predetermined distance into the blind lumen of the balloon catheter for a predetermined period of time, and removing said radiation dose delivery wire from said blind lumen of said balloon catheter after said predetermined period of time.

These and other advantages will become apparent from the detailed description, accompanying the claims and attached drawing figures.

DETAILED DESCRIPTION OF THE DRAWINGS

According to one aspect of the present invention, an apparatus guided by a guidewire within a patient's artery for reducing restenosis after arterial intervention in the patient's artery is provided, comprising a radiation dose delivery wire with a radiation source encapsulated within its distal end, and a balloon catheter with a blind lumen sealed at its distal end and a guidewire lumen extending therethrough to accept said guidewire, said blind lumen being adapted to accept said radiation delivery wire into its proximal end.

The apparatus may further comprise means for providing a liquid-tight seal between the radiation dose delivery wire and the proximal end of the blind lumen.

The means for providing a liquid-tight seal may comprise a liquid-tight radiation delivery wire port connected to the proximal end of the blind lumen, whereby a liquid-tight seal is effectuated between the proximal end of the blind lumen and the radiation dose delivery wire. Alternatively, the means for providing a liquid-tight seal may effectuate a liquid-tight seal between the proximal end of the blind lumen and an after-loader which drives the radiation dose delivery wire.

The radiation source may be a pellet, a wire, or an encapsulated radiation source, such as a paste of $Ir^{192}$, $I^{125}$, or $Pd^{103}$. Alternatively, the radiation source may be a $\gamma$-radiation emitting isotope. The length of the radiation source is determined by the length of the segment of diseased vessel, that is, the segment of vessel which is to receive a dose of radiation. The radiation source may be 0.5 to 5 cm in length and it may comprise a plurality of radioactive pellets forming a linear array.

The apparatus may further comprise means for moving the distal end of said radiation dose delivery wire to a predetermined position within said blind lumen for a predetermined period of time. The means for moving may be a computer controlled afterloader. The computer controlled afterloader may calculate said predetermined position and said predetermined time.

The computer controlled afterloader may further calculate said predetermined position and said predetermined time based upon a plurality of input variables including a half-life of the radiation source, an activity level of the radiation source, an angiograghic or ultrasound determined diameter of said artery, and a desired radiation dosage to be delivered to the artery at the predetermined position. A user may input a plurality of values each representing respective ones of the plurality of input variables to the computer controlled afterloader. The computer controlled afterloader may oscillate said distal end of said radiation dose delivery wire back and forth in the area of the predetermined position for a predetermined period of time.

An outer diameter of the guidewire and an outer diameter of the radiation dose delivery wire may be substantially equal to 0.014 inch. The radiation source may have a radioactivity of less than about 10 Curies.

The apparatus may further comprise a radiation blocking shield movable between the radiation source within the patient's artery and a user of the apparatus. The radiation blocking shield may be concrete or lead.

According to another aspect of the present invention, an apparatus inserted into a sheath in a patient's artery and guided by a guidewire within the patient's artery for reducing restenosis after arterial intervention in the patient's artery is provided, comprising a radiation dose delivery wire with a radiation source encapsulated within its distal end, and a balloon catheter with a blind lumen sealed at its distal end and a guidewire lumen extending therethrough to accept said guidewire, said blind lumen being adapted to accept said radiation dose delivery wire into its proximal end, said balloon catheter being adapted to be inserted into said sheath.

The apparatus may further comprise means for providing a liquid-tight seal between the radiation dose delivery wire and the proximal end of the blind lumen.

The apparatus may further comprise means for maintaining an extended coaxial relationship between the proximal end of said sheath and the proximal end of said blind lumen.

According to another aspect of the present invention, an apparatus guided by a guidewire within a patient's artery for reducing restenosis after arterial intervention in the patient's artery is provided, comprising a radiation dose delivery wire with a radiation source encapsulated within its distal end, and a balloon catheter with a blind lumen sealed at its distal end and a guidewire lumen extending partially through said balloon catheter, said blind lumen being adapted to accept said radiation dose delivery wire into its proximal end, said guidewire lumen having an entry port located at a distal end of said balloon catheter and an exit port located upon a circumferential surface of said balloon catheter.

According to another aspect of the present invention, an apparatus for reducing restenosis after arterial intervention in a patient's artery is provided, comprising a guidewire for insertion into the patient's artery at least as far as a target area of the artery, a radiation dose delivery wire with a radiation source encapsulated within its distal end, and a balloon catheter with a blind lumen sealed at its distal end and a guidewire lumen extending therethrough to accept said guidewire, said blind lumen being adapted to accept said radiation delivery wire into its proximal end.

According to another aspect of the present invention, an apparatus guided by a guidewire within a patient's artery for reducing restenosis after arterial intervention in the patient's artery is provided, comprising a radiation dose delivery wire with a radiation source encapsulated within its distal end, and a catheter with a blind lumen sealed at its distal end and a guidewire lumen extending therethrough to accept said guidewire, said blind lumen being adapted to accept said radiation delivery wire into its proximal end.

The apparatus may further comprise means for providing a liquid-tight seal between the radiation dose delivery wire and the proximal end of the blind lumen.

According to another aspect of the present invention, an apparatus to be inserted into a catheter for reducing restenosis after arterial intervention in a patient's artery is provided, comprising a radiation dose delivery wire with a radiation source encapsulated within its distal end, and a blind lumen open at its proximal end and sealed at its distal end, said blind lumen being adapted to accept said radiation dose delivery wire into its proximal end and to be inserted into said catheter.

The apparatus may further comprise means for providing a liquid-tight seal between the radiation dose delivery wire and the proximal end of the blind lumen.

According to another aspect of the present invention, a method of reducing restenosis after arterial intervention in a patient's artery is provided, comprising inserting a guidewire into the patient's artery until a distal end of the guidewire is at least as far into the artery as a predetermined section of the artery, inserting the guidewire into a guidewire lumen of a balloon catheter with a blind lumen, inserting the balloon catheter with the blind lumen into the patient's artery at least as far as the predetermined section of the artery, inserting a radiation dose delivery wire into said blind lumen in said balloon catheter, moving said radiation dose delivery wire a predetermined distance into the blind lumen of the balloon catheter for a predetermined period of time, and removing said radiation dose delivery wire from said blind lumen of said balloon catheter after said predetermined period of time.

The method of moving said radiation dose delivery wire a predetermined distance into the blind lumen of the balloon catheter for a predetermined period of time may result in the distal end of the radiation dose delivery wire being adjacent said predetermined section of artery.

The method of moving said radiation dose delivery wire a predetermined distance into the blind lumen of the balloon catheter for a predetermined period of time may further comprise determining where the predetermined section of artery is, determining a diameter of said predetermined section of artery, and determining a desired radiation dosage to be delivered to the predetermined section of artery. The diameter may be determined by an angiograghic or ultrasound procedure.

The method of moving said radiation dose delivery wire a predetermined distance into the blind lumen of the balloon catheter for a predetermined period of time may further comprise oscillating said radiation dose delivery wire back and forth when said distal end of radiation dose delivery wire is substantially adjacent said predetermined section of artery.

Figure 2:
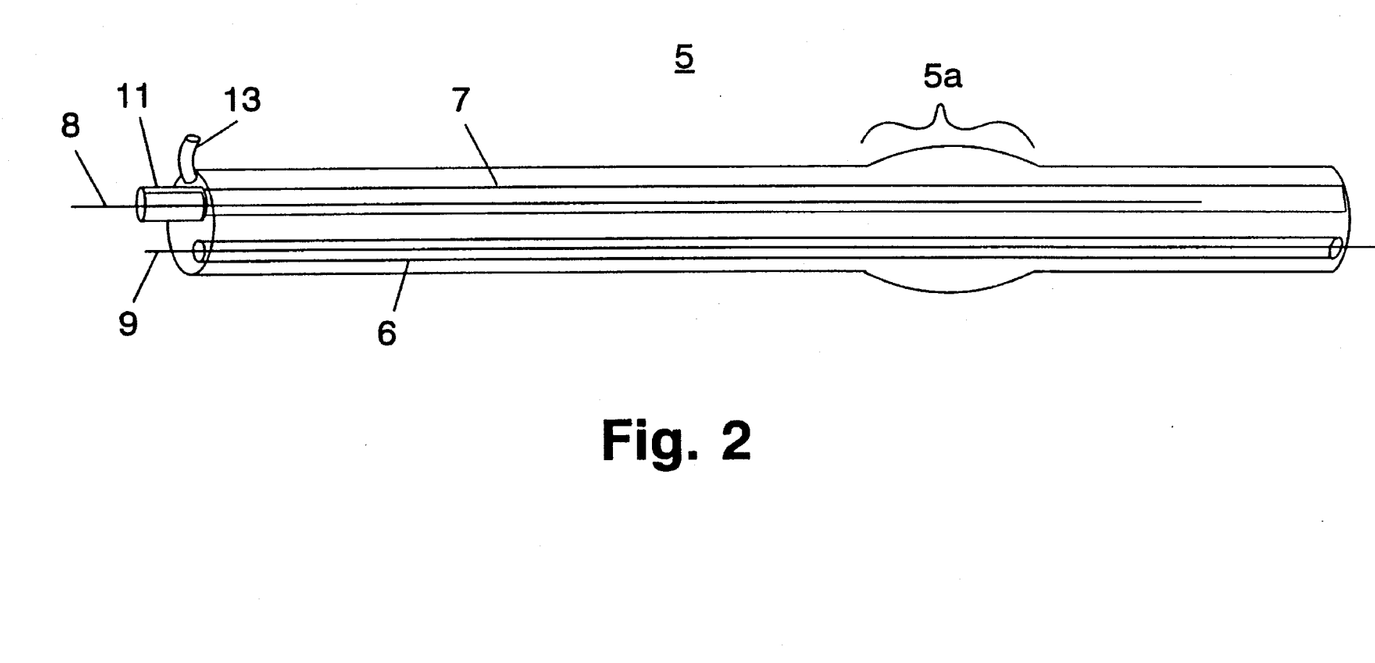
FIG. 2, shows the construction of a balloon catheter according to a first embodiment of the present invention.

Referring now to the FIGS., FIG. 2 shows a balloon catheter according to a first embodiment of the present invention, which can be used to perform the method according to the present invention. The apparatus is particularly suited for delivering radioactive doses to the coronary artery. The preferred embodiment will be described with reference to the coronary artery, but this is by way of example, and not limitation, as the present invention may also be used to deliver radiation to peripheral arteries.

The apparatus comprises a balloon catheter 5 with a guidewire lumen 6 extending entirely through the balloon catheter 5 and a blind lumen 7 which is closed at the distal end of the balloon catheter 5, for receiving a radiation dose delivery wire 8. The guidewire lumen 6 is sized to fit around a guidewire 9 and to allow the guidewire 9 to slide therein. The length of guidewire 9 is sufficient to allow it to extend past a target segment of the artery and it may be, for example, greater than about 110 cm for use in the coronary artery. For use in other arteries, the length of guidewire 9 may also be greater than about 110 cm or it may be less.

The outside diameters of the guidewire 9 and the radiation dose delivery wire 8 may be about 0.014 inch and in this case the inside diameters of the guidewire lumen 6 and the blind lumen 7 are slightly larger, to permit movement of the balloon catheter 5 over the guidewire 9 and movement of the radiation dose delivery wire 8 through blind lumen 7.

The radiation dose delivery wire entry port 11, at the proximal end of the balloon catheter 5, is adapted to receive the radiation dose delivery wire 8 and to provide a watertight seal. Thus, the radiation dose delivery wire 8 is isolated from contact with the patient's body fluids. The balloon inflation port 13 allows inflation of the balloon section 5a at the distal end of the balloon catheter 5 in the conventional manner.

Figure 3:
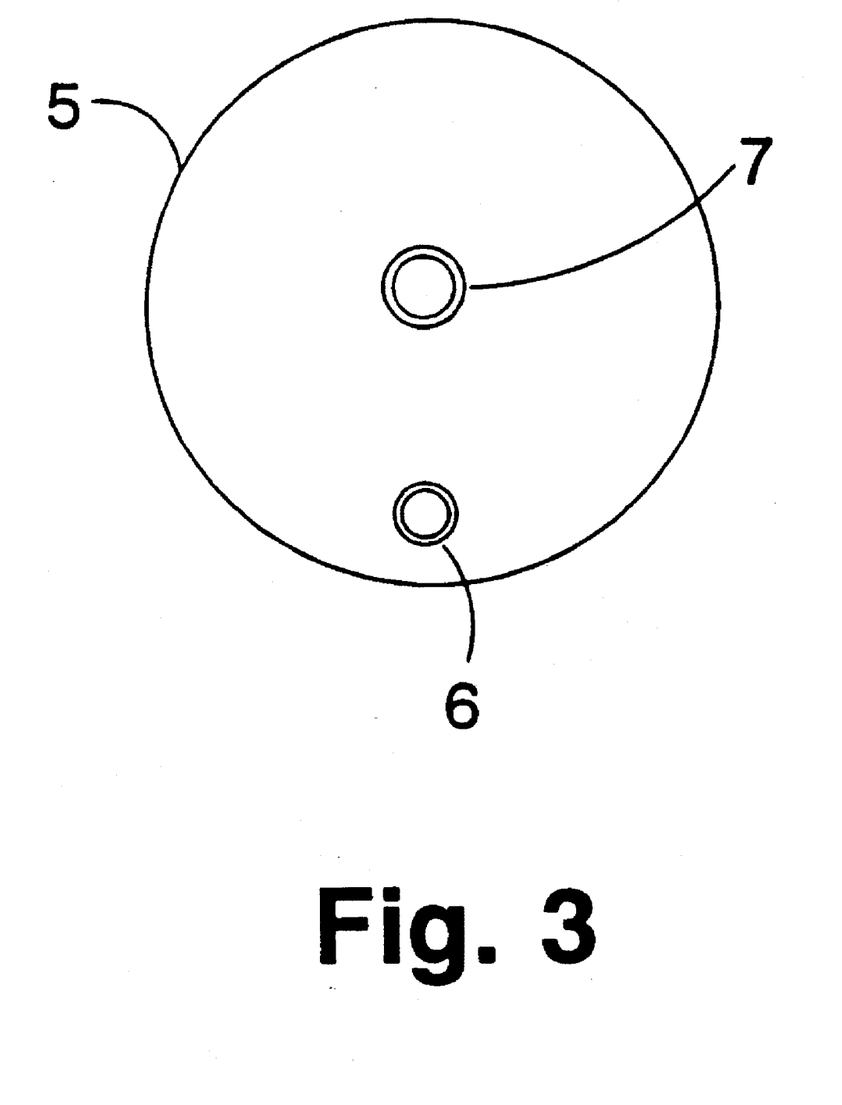
FIG. 3 shows a cross-section of the balloon catheter according to the first embodiment of the present invention.

Referring now to FIG. 3, wherein the same reference numerals of FIG. 2 are applied to the same parts and therefore do not require detailed description, it is seen that the guidewire lumen 6 may be off center with regard to the balloon catheter 5, while the blind lumen 7, which is adapted to encircle the radiation dose delivery wire 8, may be substantially in the center of the balloon catheter 5.

Figure 4:
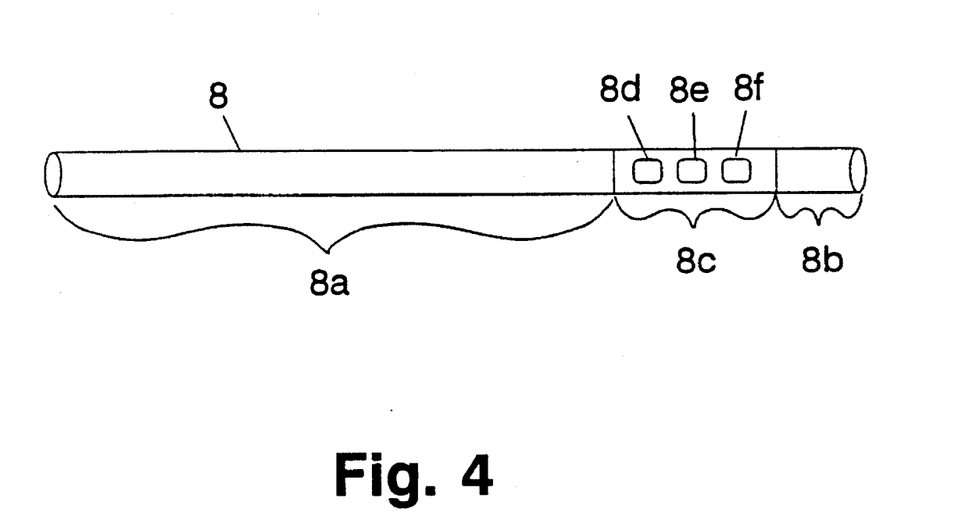
FIG. 4 shows the construction of a radiation dose delivery wire of the present invention.

Referring now to FIG. 4, wherein the same reference numerals of FIG. 2 are applied to the same parts and therefore do not require detailed description, it is seen that the radiation dose delivery wire 8 may include non-radioactive sections 8a and 8b and radioactive section 8c, which has encapsulated within the distal end of radiation dose delivery wire 8, a linear array of radioactive sources 8d, 8e, and 8f, such as pellets of $Ir^{192}$, $I^{125}$, or $Pd^{103}$. The length of the linear array of pellets may be less than or equal to about 2 cm for use in the coronary artery and less than or equal to about 10 cm for use in periphery arteries. Alternatively, the radioactive source may be composed of a non-linear array of such radioactive pellets or it may be composed of a single radioactive pellet. The radioactivity of each of the radioactive sources 8d, 8e, and 8f may be less than or equal to 10 Curies.

The operation of an apparatus to reduce restenosis after arterial intervention according to the first embodiment of the present invention is as follows. The guidewire 9 is inserted into the patient's artery. The distal end of the guidewire 9 is inserted at least as far as, and preferably past the target site, that is, the site that is to receive the dose of radiation. The guidewire 9 is then inserted into the guidewire lumen 6 and the balloon catheter 5 is moved down the guidewire towards the distal end until the balloon section 5a is adjacent the target site. In the case of a balloon angioplasty procedure the balloon section 5a is then inflated and deflated by balloon inflation/deflation inflation means (not shown) connected to the balloon inflation port 13. Alternatively, if it is desired to deliver a dose of radiation to the target area without inflating and deflating the balloon section 5a, such as following an atherectomy or other arterial intervention, the balloon section 1a need not be inflated and deflated.

Finally, the radiation dose delivery wire 8 is inserted into the proximal end of the blind lumen 7 within the balloon catheter 5 through the radiation dose delivery wire entry port 11. The radiation dose delivery wire 8 is inserted towards the distal end of the balloon catheter 5 until the radioactive sources 8d, 8e, and 8f are substantially adjacent the target area. The radioactive sources 8d, 8e, and 8f are left in place until a desired dosage of radiation has been delivered to the target area and then the radiation dose delivery wire 8 is removed from the balloon catheter 5. The length of time that the radioactive sources 8d, 8e, and 8f are left adjacent the target area depends upon the activity of the radioactive sources 8d, 8e, and 8e, the diameter of the artery at the target area, and the desired dosage to be delivered. It should be noted that the radiation dose delivery wire 8 may be oscillated back and forth within the blind lumen 7 so that the radioactive sources 8d, 8e, and 8f may be shorter than the target area while still being able to deliver radiation to the entire target area. In addition, if the radiation dose delivery wire 8 is oscillated back and forth, the time that the radioactive sources 8d, 8e, and 8f must be left adjacent the target area in order to deliver a desired dosage of radiation will also depend upon the length of the target area.

Alternatively, the guidewire 9 may be inserted into the artery as above and a conventional balloon catheter without a blind lumen placed over the guidewire 9 and advanced to the target area to be inflated, deflated, and removed from the artery. After removal from the artery, the balloon catheter 5 of the instant invention, with the blind lumen 7 may be placed over the guidewire 9 utilizing the guidewire lumen 6 and inserted adjacent the target area in order to allow the radiation dose delivery wire 8 to be inserted into the blind lumen 7 to deliver a dosage of radiation to the target area as described above. This procedure permits the use of a conventional balloon catheter to perform an angioplasty procedure before the balloon catheter 5 of the instant invention is utilized to deliver a dose of radiation.

Figure 5:
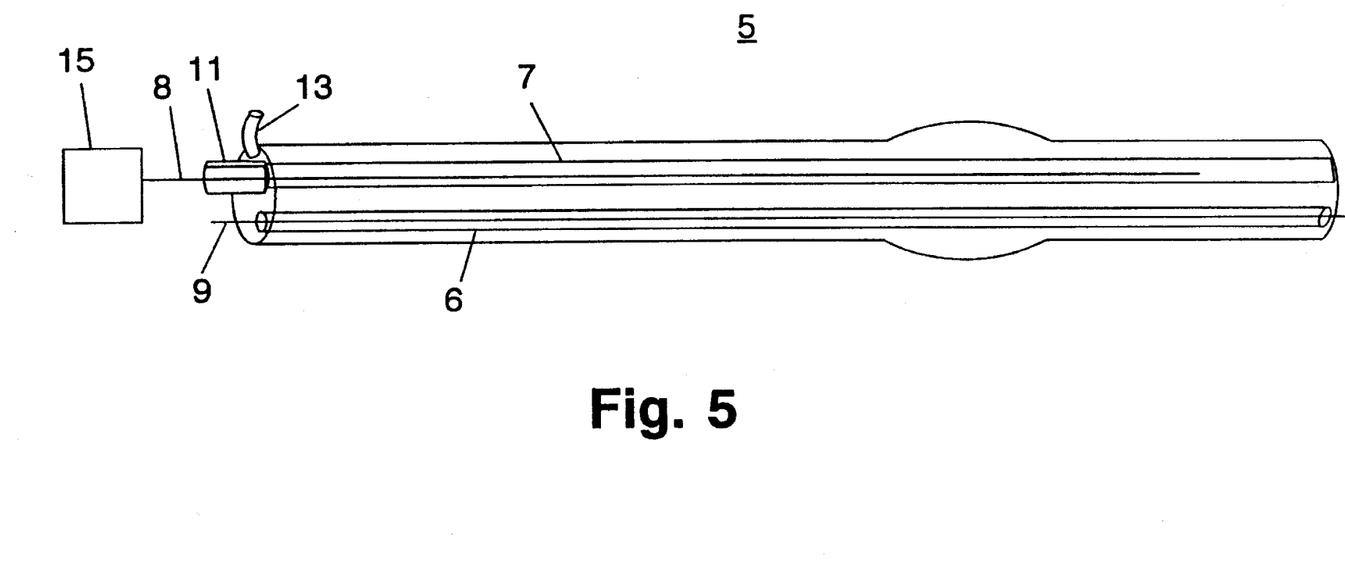
FIG. 5 shows the construction of a second embodiment of the present invention.

Referring now to FIG. 5, wherein the same reference numerals of FIG. 2 are applied to the same parts and therefore do not require detailed description, a balloon catheter according to a second embodiment of the present invention is shown, which can be used to perform the method according to the present invention. In this FIG., a computer controlled afterloader 15, similar to a conventional afterloader such as the one distributed by Nucletron Corp., of Columbia, Md., is connected to the proximal end of the radiation dose delivery wire 8 and is utilized to insert the radiation dose delivery wire 8 into the blind lumen 7 until the radioactive sources 8d, 8e, and 8f are adjacent the target area and to remove the radiation dose delivery wire 8 from the blind lumen 7 after a predetermined dosage of radiation has been delivered to the target area.

The computer controlled afterloader 15 of the present invention differs from the conventional afterloader in that the computer controlled afterloader 15 of the present invention allows an operator to input variables representing the activity of the radioactive sources 8d, 8e, and 8f, the date that the radioactive sources 8d, 8e, and 8f are being delivered adjacent the target area (to take into account decay of the radioactive sources 8d, 8e, and 8f), the diameter of the artery at the target area, the length of the target area, and the value of the desired radioactive dose to be delivered to the target area. The computer controlled afterloader 15 then calculates the time that the radioactive sources 8d, 8e, and 8f must be adjacent the target area to deliver the desired radioactive dosage and then moves the radiation dose delivery wire 8 towards the distal end of the balloon catheter 5 until the radioactive sources 8d, 8e, and 8f are adjacent the target area, waits the calculated time, and then pulls the radiation dose wire 8 back out of the balloon catheter 5.

In addition, the computer controlled afterloader 15 may oscillate the radiation dose delivery wire 8 back and forth while the radioactive sources 8d, 8e, and 8f are adjacent the target area. In this case the computer controlled afterloader 15 would take into account the length of the target area and the rate of oscillation in determining the time necessary to deliver the desired dosage.

The computer controlled afterloader 15 may include a program memory for storing a program to calculate the length of time that the radioactive sources 8d, 8e, and 8f must be adjacent the target area to deliver a desired dosage of radiation, a power supply backup, and a database memory for storing the number of times that a particular radioactive source has been used.

Figure 6:
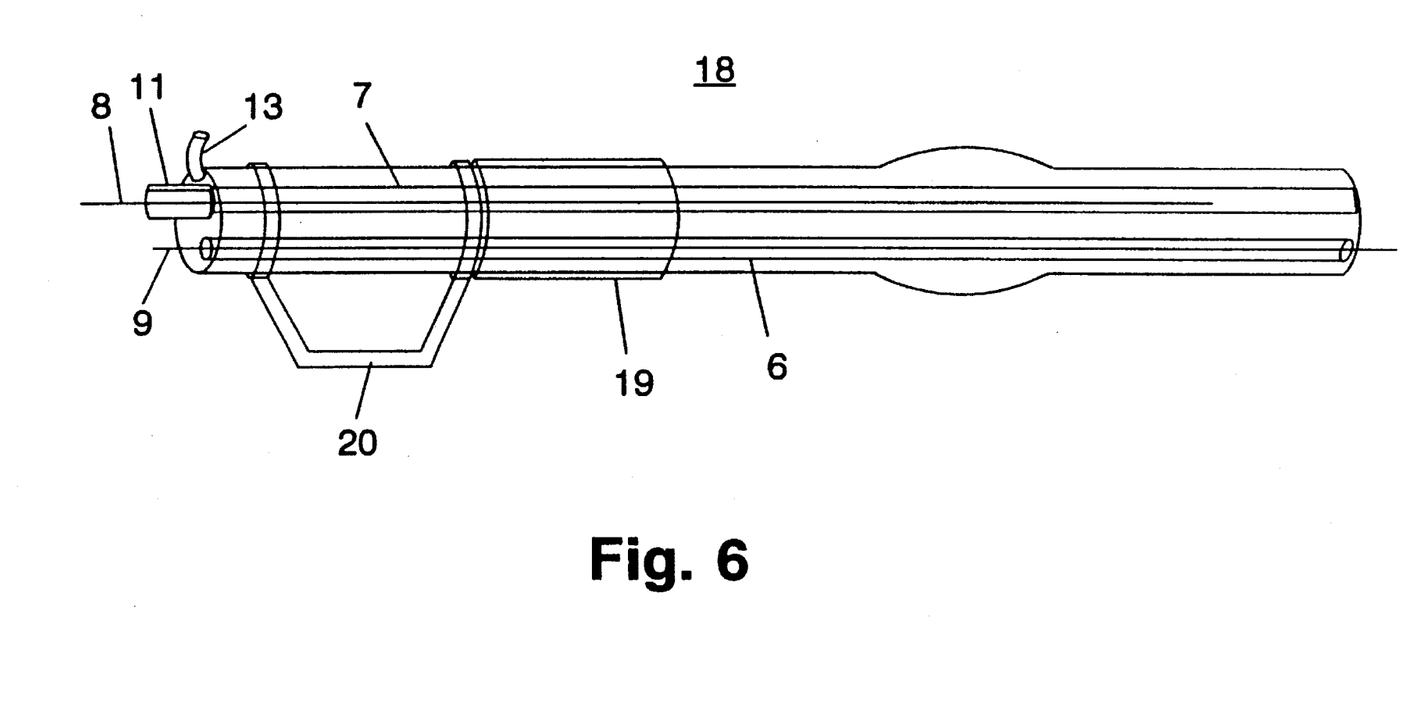
FIG. 6 shows the construction of a third embodiment of the present invention.

Referring now to FIG. 6, wherein the same reference numerals of FIG. 2 are applied to the same parts and therefore do not require detailed description, a balloon catheter 18 according to a third embodiment of the present invention is shown, which can be used to perform the method according to the present invention. A clamp 20 may be utilized to maintain an extended coaxial position between the radiation dose delivery wire entry port 11 connected to the proximal end of the blind lumen 7 and a proximal end of a sheath 19, which surrounds catheter 18 at the area of the incision in the patient's body, during insertion of the radiation dose delivery wire 8 into the blind lumen 7.

Figure 7:
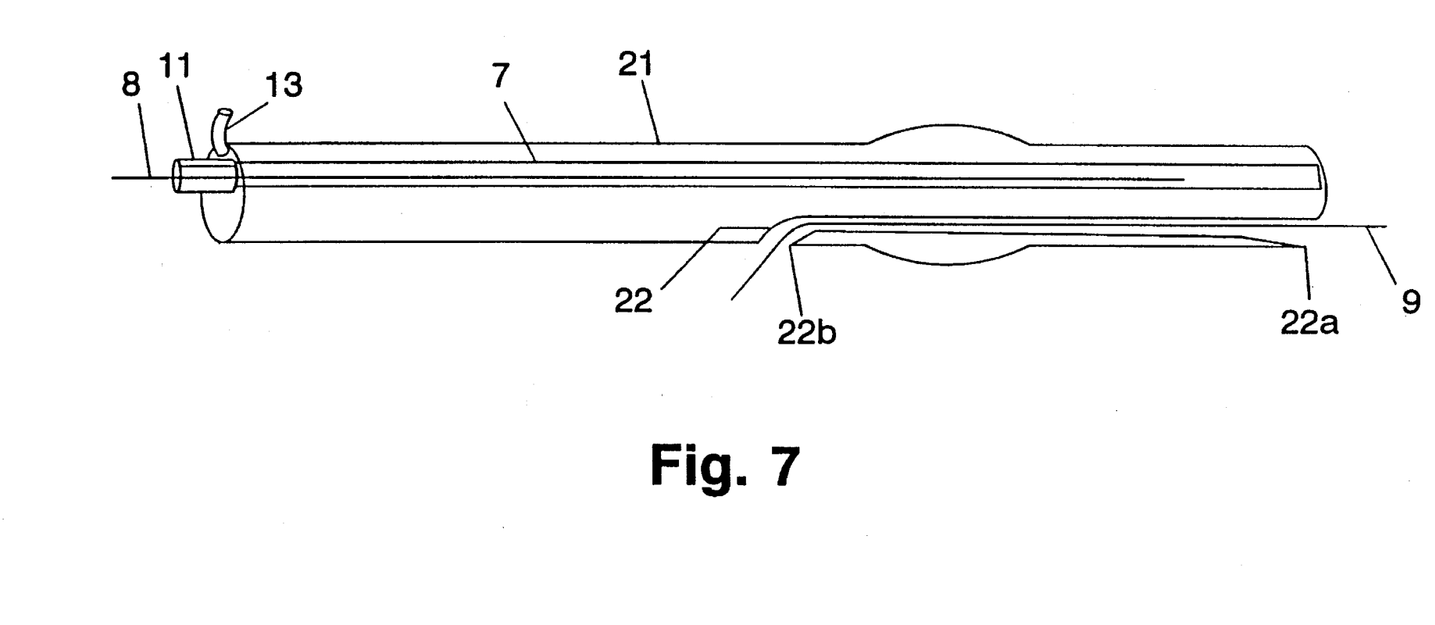
FIG. 7 shows the construction of a fourth embodiment of the present invention.

Referring now to FIG. 7, wherein the same reference numerals of FIG. 2 are applied to the same parts and therefore do not require detailed description, a balloon catheter 21 according to a fourth embodiment of the present invention is shown, which can be used to perform the method according to the present invention. In this FIG., a guidewire lumen 22 extends for a distance less than the length of the balloon catheter 21. That is, the guidewire lumen 22 has an entry point 22a at the distal end of balloon catheter 21 and exit point 22b along the length of balloon catheter 21, rather than at its proximal end.

As in the first embodiment, the guidewire 9 is inserted into the artery and the guidewire lumen 22 guides the balloon catheter 21 towards the distal end of the guidewire 9. Also, as in the first embodiment, the radiation dose delivery wire 8 rides within the blind lumen 23 of the balloon catheter 21.

Figure 8:
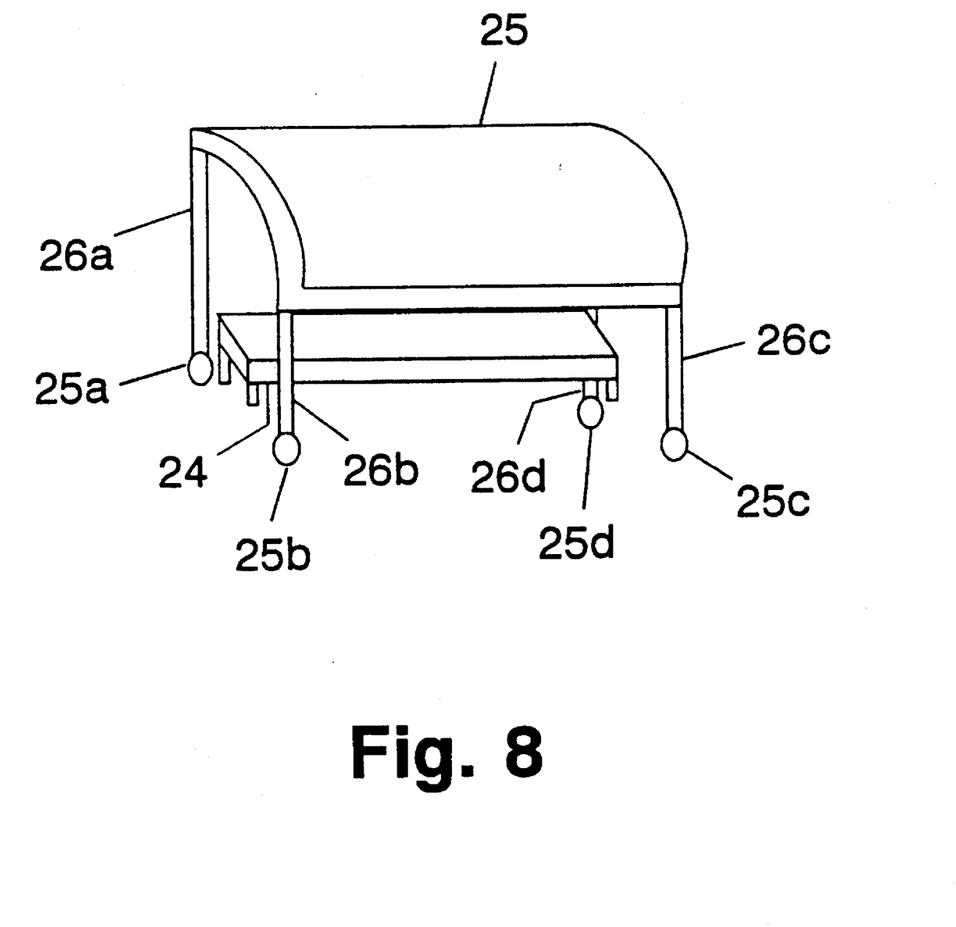
FIG. 8 shows the construction of a fifth embodiment of the present invention.

Referring now to FIG. 8, wherein the same reference numerals of FIG. 2 are applied to the same parts and therefore do not require detailed description, an apparatus according to a fifth embodiment of the present invention is shown, which can be used to perform the method according to the present invention. In this FIG., a radiation shield 25 is movable and is adapted to be moved between a patient (not shown) on a support 24 and an operator of the apparatus (not shown). The radiation shield 25 may, for example, be moveable by means of rollers 25a, 25b, 25c, and 25d mounted to legs 26a, 26b, 26c, and 26d.

In operation the balloon catheter 5, not shown in this FIG., is inserted into a patient (not shown) who is supported by the support 24 and the radiation shield 25 is moved between an operator of the apparatus and the radiation source 8d, 8e, and 8f within the blind lumen 7 of the balloon catheter 5. The radiation shield 25 is thus adaptable for different sized patients because it is movable and it therefore provides protection to the doctor and other staff from over-exposure to radiation.

Figure 9:
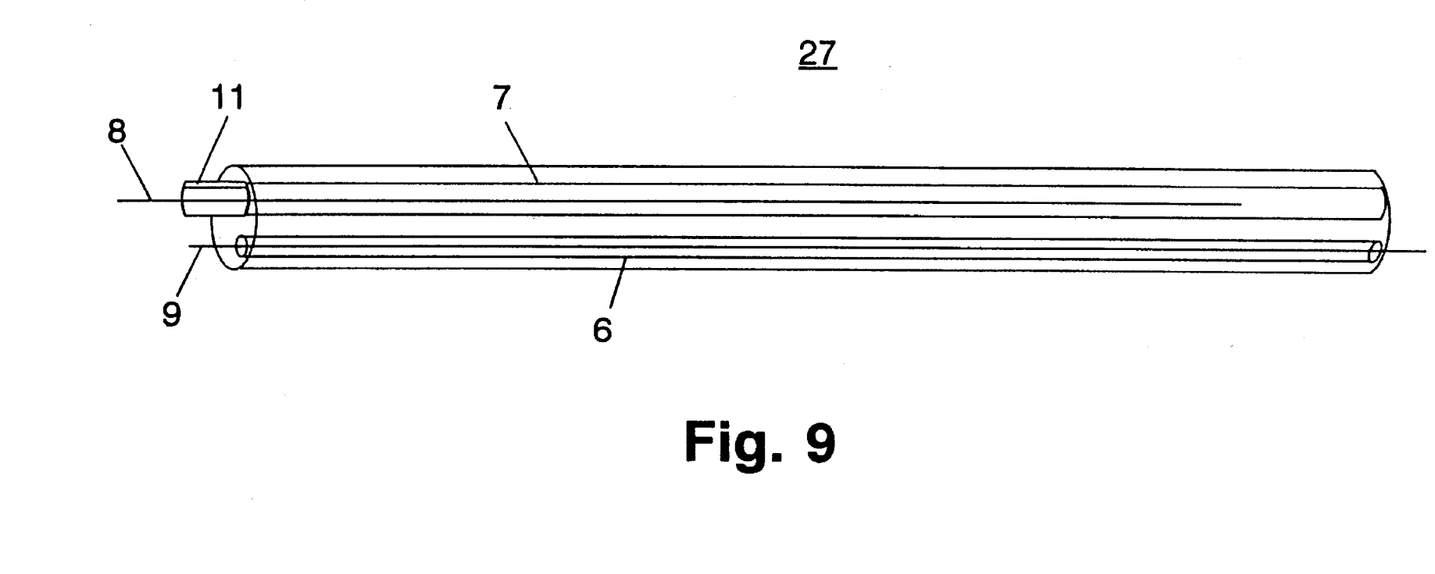
FIG. 9 shows the construction of a sixth embodiment of the present invention.

Referring now to FIG. 9, wherein the same reference numerals of FIG. 2 are applied to the same parts and therefore do not require detailed description, an apparatus according to a sixth embodiment of the present invention is shown, which can be used to perform the method according to the present invention. In this FIG., a catheter without a balloon 27 includes blind lumen 7 and guidewire lumen 6. This embodiment is utilized in a fashion similar to the first embodiment, except here, the apparatus is used only to deliver radiation, and does not have the balloon function of the first embodiment.

Figure 10:
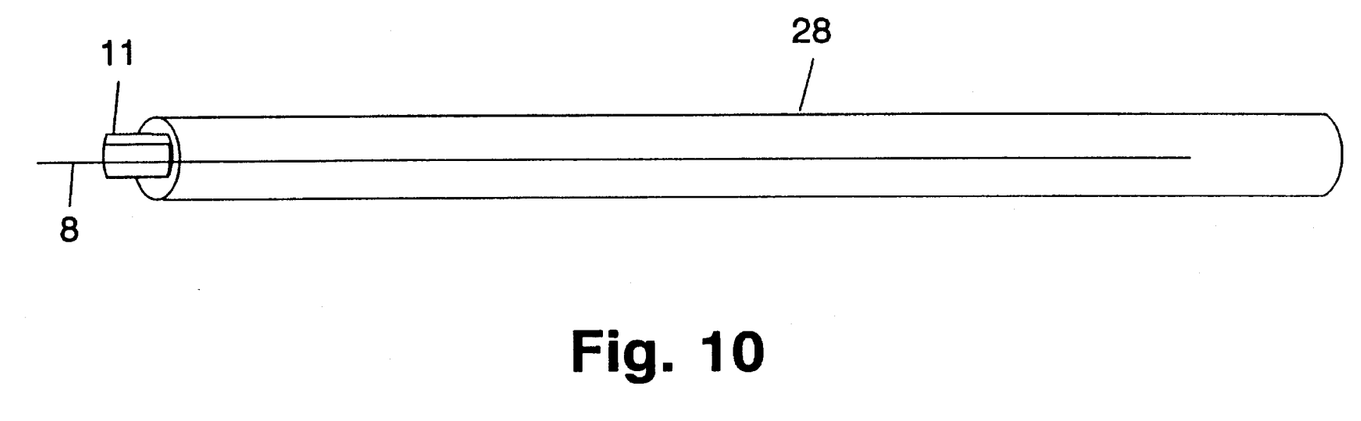
FIG. 10 shows the construction of a seventh embodiment of the present Invention.

Referring now to FIG. 10, wherein the same reference numerals of FIG. 2 are applied to the same parts and therefore do not require detailed description, an apparatus according to a seventh embodiment of the present invention is shown, which can be used to perform the method according to the present invention. In this FIG., a blind lumen 28, which accepts radiation dose delivery wire 8 into its proximal end through radiation dose delivery wire entry port 11, is adapted to be removably inserted into a catheter (not shown). The catheter may be a balloon type catheter or it may be a catheter without a balloon.

In operation, the catheter is inserted into a patient in the conventional manner. Blind lumen 28 is then inserted into the catheter and, as in the first embodiment, the radiation dose delivery wire 8 is advanced into the blind lumen 28, through the radiation dose deliver wire entry port 11, until the distal end of the radiation dose delivery wire 8 is adjacent the segment of artery that is to receive a radioactive dose. Also, as in the first embodiment, the radiation dose delivery wire 8 is withdrawn after a desired dose of radiation has been delivered to the artery segment. This embodiment is intended primarily, but not exclusively, for procedures in the peripheral vascular areas.

It must be noted that although the present invention is described by reference to particular embodiments thereof, many changes and modifications of the invention may become apparent to those skilled in the art without departing from the spirit and scope of the invention as set forth in the claims.

What is claimed is:

1. An apparatus for use with a guidewire for reducing restenosis after arterial intervention in a patient's artery comprising:

a radiation dose delivery wire with a radiation source encapsulated within its distal end; and a balloon catheter with a blind lumen sealed at its distal end and a guidewire lumen extending therethrough adapted to accept a guidewire for guiding the balloon catheter in the patient's artery;

said blind lumen being adapted to accept said radiation dose delivery wire into its proximal end.

2. The apparatus of claim 1, further comprising means for providing a liquid-tight seal between the radiation dose delivery wire and the proximal end of the blind lumen.

3. The apparatus of claim 2, wherein said means for providing a liquid-tight seal comprises a liquid-tight radiation delivery wire port connected to the proximal end of the blind lumen, whereby a liquid-tight seal is effectuated between the proximal end of the blind lumen and the radiation dose delivery wire.

4. The apparatus of claim 1, wherein said radiation source is a pellet of $Ir^{192}$.

5. The apparatus of claim 1, wherein said radiation source is a pellet of $I^{125}$.

6. The apparatus of claim 1, wherein said radiation source is a pellet of $Pd^{103}$.

7. The apparatus of claim 1, wherein said radiation source comprises a plurality of radioactive pellets forming a linear array.

8. The apparatus of claim 7, wherein said linear array is between 0.5 and 5 cm long.

9. The apparatus of claim 1, wherein an outer diameter of the guidewire and an outer diameter of the radiation dose delivery wire are substantially equal to 0.014 inch.

10. The apparatus of claim 1, wherein the radiation source has a radioactivity of less than about 10 Curies.

11. An apparatus for use with a sheath and a guidewire for reducing restenosis after arterial intervention in a patient's artery comprising:

a radiation dose delivery wire with a radiation source encapsulated within its distal end; and a balloon catheter with a blind lumen sealed at its distal end and a guidewire lumen extending therethrough adapted to accept a guidewire for guiding the balloon catheter in the patient's artery;

said blind lumen being adapted to accept said radiation dose delivery wire into its proximal end;

said balloon catheter being adapted to be inserted into a sheath in the patient's artery surrounding said guidewire.

12. The apparatus of claim 11, further comprising means for providing a liquid-tight seal between the radiation dose delivery wire and the proximal end of the blind lumen.

13. An apparatus for reducing restenosis after arterial intervention in a patient's artery comprising:

a guidewire for insertion into the patient's artery at least as far as a target area of the artery;

a radiation dose delivery wire with a radiation source encapsulated within its distal end; and a balloon catheter with a blind lumen sealed at its distal end and a guidewire lumen extending therethrough to accept said guidewire;

said blind lumen being adapted to accept said radiation delivery wire into its proximal end.

14. A method of reducing restenosis after arterial intervention in a patient's artery, comprising:

inserting a guidewire into the patient's artery until a distal end of the guidewire is at least as far into the artery as a predetermined section of the artery;

inserting the guidewire into a guidewire lumen of a balloon catheter with a blind lumen;

inserting the balloon catheter with the blind lumen into the patient's artery at least as far as the predetermined section of the artery;

inserting a radiation dose delivery wire into said blind lumen in said balloon catheter;

moving said radiation dose delivery wire a predetermined distance into the blind lumen of the balloon catheter for a predetermined period of time; and removing said radiation dose delivery wire from said blind lumen of said balloon catheter after said predetermined period of time.

15. The method of claim 14, wherein said step of moving said radiation dose delivery wire a predetermined distance into the blind lumen of the balloon catheter for a predetermined period of time results in the distal end of the radiation dose delivery wire being adjacent said predetermined section of artery.

16. The method of claim 15, wherein said step of moving said radiation dose delivery wire a predetermined distance into the blind lumen of the balloon catheter for a predetermined period of time further comprises determining where the predetermined section of artery is, determining a diameter of said predetermined section of artery, and determining a desired radiation dosage to be delivered to the predetermined section of artery.

17. The method of claim 16, wherein said step of moving said radiation dose delivery wire a predetermined distance into the blind lumen of the balloon catheter for a predetermined period of time further comprises moving said radiation dose delivery wire back and forth when said distal end of said radiation dose delivery wire is substantially adjacent said predetermined section of artery.

* * * * *